United States Patent
Yang et al.

(10) Patent No.: US 8,624,073 B1
(45) Date of Patent: Jan. 7, 2014

(54) HOMOGENEOUS CATALYSTS FOR BIODIESEL PRODUCTION

(71) Applicants: Shih-Chieh Yang, Chiayi (TW); Jen-Ray Chang, Chiayi (TW); Maw-Tien Lee, Chiayi (TW); Tzong-Bin Lin, Chiayi (TW); Fu-Ming Lee, Katy, TX (US); Cheng-Tsung Hong, Chiayi (TW); Jeng-Cheng Lee, Chiayi (TW)

(72) Inventors: Shih-Chieh Yang, Chiayi (TW); Jen-Ray Chang, Chiayi (TW); Maw-Tien Lee, Chiayi (TW); Tzong-Bin Lin, Chiayi (TW); Fu-Ming Lee, Katy, TX (US); Cheng-Tsung Hong, Chiayi (TW); Jeng-Cheng Lee, Chiayi (TW)

(73) Assignee: CPC Corporation, Taiwan, Taipei (TW)

( * ) Notice: Subject to any disclaimer, the term of this patent is extended or adjusted under 35 U.S.C. 154(b) by 0 days.

(21) Appl. No.: 13/759,644

(22) Filed: Feb. 5, 2013

(51) Int. Cl.
  *C07C 1/00* (2006.01)
  *C11C 3/00* (2006.01)

(52) U.S. Cl.
  USPC ................. 585/240; 44/605; 554/174

(58) Field of Classification Search
  USPC ............. 585/240; 44/605; 554/170, 174, 198; 502/171
  See application file for complete search history.

(56) References Cited

U.S. PATENT DOCUMENTS

| | | | |
|---|---|---|---|
| 2,360,844 A | 10/1944 | Bradshaw et al. | |
| 4,042,771 A | 8/1977 | Avaro et al. | |
| 4,698,186 A | 10/1987 | Jeromin et al. | |
| 7,906,665 B2 * | 3/2011 | Lin et al. | 554/167 |
| 8,030,257 B2 | 10/2011 | Habeeb et al. | |
| 8,063,232 B2 * | 11/2011 | Hagadorn et al. | 548/402 |
| 8,227,632 B2 | 7/2012 | Berry et al. | |
| 8,314,188 B2 | 11/2012 | Rempel et al. | |
| 2007/0282118 A1 * | 12/2007 | Gupta et al. | 554/169 |
| 2009/0126262 A1 * | 5/2009 | Asthana et al. | 44/388 |
| 2010/0251605 A1 | 10/2010 | Reed et al. | |
| 2011/0035993 A1 * | 2/2011 | Loescher | 44/388 |
| 2011/0185625 A1 * | 8/2011 | Singh et al. | 44/307 |

\* cited by examiner

*Primary Examiner* — Nina Bhat
(74) *Attorney, Agent, or Firm* — Cascio & Zervas

(57) ABSTRACT

Non-basic and non-acidic homogeneous catalysts organometallic compound of the formula: $M(OCH_3)_x$ wherein M is B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4 can catalyze transesterification of oils and fats having high free fatty acid content and with an acid number from 0.5 to 20, into biodiesel. $B(OCH_3)_3$ and $Ge(OCH_3)_4$, having low boiling points, are easily recovered from the biodiesel and glycerol phases and recycled for reuse. Continuous biodiesel production with the novel homogenous catalysts is achieved without the complicated and troublesome steps attendant with conventional processes using base or acid homogeneous catalyst. The high purity biodiesel is produced without acid-base neutralization, water wash, filtration, and solid disposal steps for removing the spent catalyst from the product streams associated with prior techniques.

22 Claims, 3 Drawing Sheets

HOMOGENEOUS CATALYSTS FOR BIODIESEL PRODUCTION

FIELD OF THE INVENTION

The present invention relates generally to biodiesel production through transesterfication of vegetable oils and animal fats with non-basic, non-acidic homogeneous organo-metallic catalysts having the general formula $M(OCH_3)_x$ wherein M is a selected metal.

BACKGROUND OF THE INVENTION

Biodiesel is produced commercially from vegetable oils and/or animal fat through transesterification with alcohol to convert triglycerides into alkyl esters of the fatty acids (biodiesel) and glycerol using a basic homogeneous catalyst, such as sodium hydroxide, potassium hydroxide, and sodium acetate. Because base-catalyzed reactions are very sensitive to the presence of free fatty acids (FFAs), they are unsuitable for unrefined oils with FFA contents higher than about 3%. Moreover, to prevent saponification during the transesterification reaction, FFA and water contents in the oil feed should be less than 0.5 and 0.05 wt %, respectively, which means that essentially only pure vegetable oils can be used. High FFA levels in the oil feed also deplete the base catalyst through acid-base neutralization reactions. Base-catalyzed reactions also require that the NaOH catalyst be neutralized with acid and removed from the reactor effluent with a water wash. The resulting salt byproduct from the acid/base neutralization must then be separated from the biodiesel product. Finally, water produced in the reaction promotes saponification of the fatty acids with the NaOH catalyst which renders phase separations among the products (biodiesel and glycerol) and the salts even more difficult.

Homogeneous acid catalysts have also been employed in transesterification reactions for biodiesel production but acid-catalyzed reactions are slow and generally less suitable for large scale operations. Although the performance of the acid catalyst is not affected by the presence of FFA in the oil or fat feedstock, nevertheless, the process requires a high alcohol-to-oil mole ratio and long reaction times due to the low activity of the acid catalyst. When using a base or an acid catalyst, the transesterification process, which occurs in a corrosive environment, requires costly neutralization, water wash, filtration, and solid waste disposal steps to remove the spent catalyst from the biodiesel and glycerol product streams.

SUMMARY OF THE INVENTION

The present invention is directed to neutral, non-corrosive homogeneous catalysts for transesterification of triglycerides through a non-basic, non-acidic reaction mechanism. The inventive techniques can be implemented in a simple, inexpensive process that does not require the troublesome neutralization, water wash, filtration, and solid disposal operations for spent catalyst removal associated with conventional transesterification techniques using base or acid catalysts. The non-basic, non-acidic homogeneous catalysts are organo-metallic compounds containing at least one —$OCH_3$ functional group for effectively catalyzing the transesterification and esterification reactions simultaneously for directly producing biodiesel from the vegetable oils, animal oils and fats or waste cooking oils having high FFA content.

In one aspect, the invention is directed to a process for producing biodiesel through transesterification that includes: contacting a triglyceride-containing vegetable or animal oil with an aliphatic mono-alcohol containing 1 to 6 carbon atoms and a homogenous catalyst to effect transesterification to yield a mixture containing a fatty acid alkyl ester and glycerol wherein the homogenous catalyst is a non-basic, non-acidic organo-metallic compound having the formula: $M(OCH_3)_x$ wherein M is metal that is selected from the group consisting of B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4.

In a further aspect, the invention is directed to a continuous process for producing biodiesel through transesterification which includes:

a. introducing an oil feed and a first alcohol/catalyst mixture, which comprises an aliphatic mono-alcohol containing 1 to 6 carbon atoms and a homogenous catalyst that is a non-basic, non-acidic organo-metallic compound having the formula: $M(OCH_3)_x$ wherein M is metal that is selected from the group consisting of B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4, into a first reactor to effect transesterification to yield a first effluent containing a fatty acid alkyl ester, glycerol, alcohol and homogenous catalyst;

b. removing alcohol and homogenous catalyst from the first effluent and recovering a first biodiesel phase comprising the fatty acid alkyl ester and a first glycerol phase;

c. introducing the first biodiesel phase, a second alcohol/catalyst mixture which comprises the aliphatic mono-alcohol and the homogenous catalyst, and optionally fresh alcohol and optionally fresh homogenous catalyst into a second reactor to effect transesterification to yield a second effluent containing the fatty acid alkyl ester, glycerol, alcohol and homogenous catalyst; and d. removing alcohol and homogenous catalyst from the second effluent and recovering a purified biodiesel phase comprising the fatty acid alkyl ester and a second glycerol phase.

$B(OCH_3)_3$ and $Ge(OCH_3)_4$ catalysts having low boiling point of 68° C. and 66° C., respectively, are particularly suited for continuous transesterification processes since these catalysts can be easily recovered from the biodiesel and glycerol streams and recycled for reuse.

DETAILED DESCRIPTION OF THE INVENTION

Figure 1:
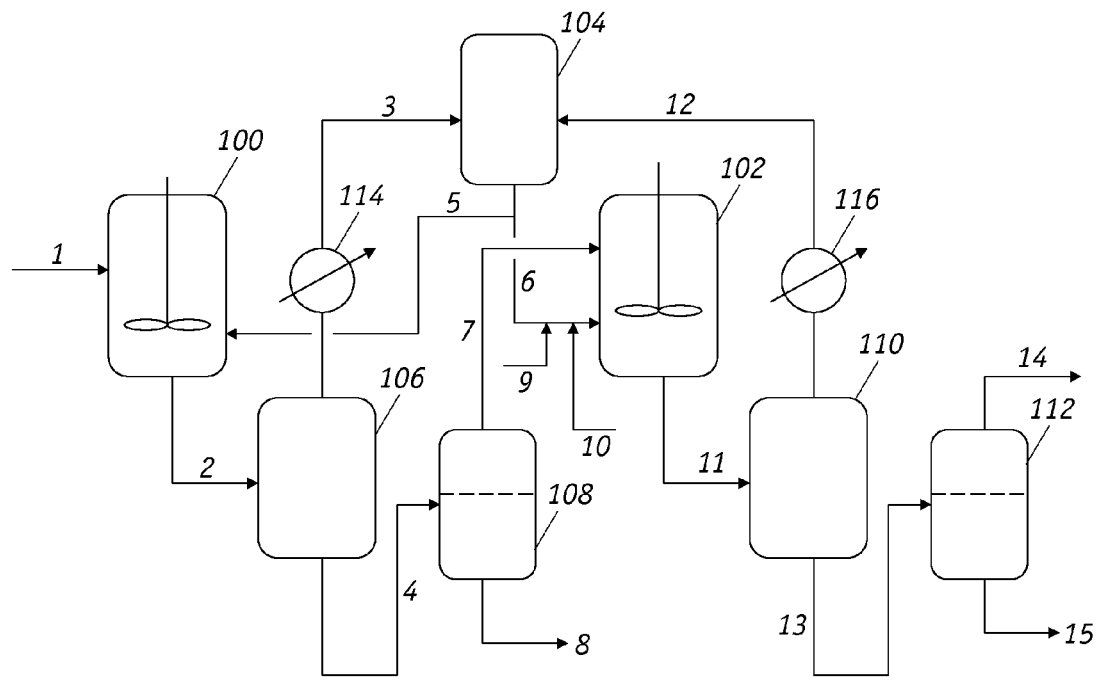
FIGS. 1 and 2 show continuous biodiesel production processes employing (i) two continuous stirred tank reactors in series and (ii) two continuous tubular reactors (packed with static mixer) in series, respectively.

The present invention is based in part on the demonstration that the weak base, potassium tetrahydroboron ($KBH_4$) is capable of catalyzing the transesterification reaction between soybean oil and methanol ($CH_3OH$) to produce methyl ester of the fatty acids (the biodiesel) with an activity that is comparable to that of conventional homogeneous NaOH (or KOH) catalyst. It is known that the $KBH_4$ reacts with $CH_3OH$ to form potassium tetramethoxyborate ($KB(OCH_3)_4$). From this initial observation concerning $KBH_4$, the following reaction mechanisms are postulated:

  (1)

  (2)

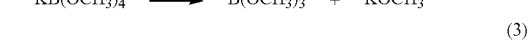  (3)

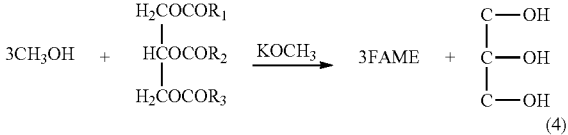  (4)

In Reaction (1), $KBH_4$ and $CH_3OH$ form $KB(OCH_3)_4$ which decomposes into $B(OCH_3)_3$ and $KOCH_3$ as depicted in Reaction (2). The presence of $B(OCH_3)_3$ in an reactor effluent was confirmed by gas chromatographic-mass (GC-Mass) analysis whereas $KOCH_3$ was not detected. This is likely due to the basic nature of $KOCH_3$ and its propensity to disassociate into $K^+$ and $OCH_3^-$ species through a mechanism that is similar that of the basic KOH catalyst. It is expected that Reactions (1) and (2) occur and both $B(OCH_3)_3$ and $KOCH_3$ catalyze the transesterification reactions between soybean oil and methanol, according to Reactions (3) and (4), to produce fatty acid methyl ester (FAME) and glycerol, in each reaction.

To evaluate the feasibility of using $B(OCH_3)_3$ to catalyze transesterification reactions, a mixture of vegetable oil and methanol, with an oil-to-alcohol mole ratio of 1:6, was mixed with 5 wt % amount of $B(OCH_3)_3$ and introduced to an autoclave. The autoclave was operated at a pressure of 14.6 bar to carry out the batch transesterification reaction at temperatures ranging from 130 to 230° C. The reaction time was two hours. After the reaction, the content was analyzed for conversion and selectivity of the catalyst. It was found that $B(OCH_3)_3$ exhibited significant activity and selectivity for catalyzing the transesterification reaction between the vegetable oil and methanol. Since the catalyst was not consumed it can be recycled for reuse. When it is incorporated into continuous processes, the catalyst performance can be enhanced by increasing the catalyst and alcohol circulation rate to at least match the performance of the conventional homogeneous base catalyst, including the highly active NaOH or KOH catalyst.

It was further demonstrated that other organo-metallic compounds containing the —$OCH_3$ functional groups, e.g., ($M(OCH_3)_x$), exhibited activity for catalyzing transesterification reactions. $Ti(OCH_3)_4$, $Sb(OCH_3)_4$, $Ge(OCH_3)_4$, $Al(OCH_3)_3$, and $Cu(OCH_3)_2$ were individually tested in an autoclave using the same vegetable oil and under the same conditions as for $B(OCH)_3$ set forth herein. The results showed that $Ti(OCH_3)_4$, $Sb(OCH_3)_3$, $Ge(OCH_3)_4$ exhibited high activity and selectivity at levels that are comparable to that of a basic catalyst, such as NaOH (or KOH) for catalyzing the transesterification reaction between the vegetable oil and the alcohol whereas $Al(OC_2H_5)_3$ and $Cu(OCH_3)_2$ exhibited lower activity and selectivity. The selection of suitable homogeneous catalysts for continuous processes may also depend on their physical properties some which are listed in Table 1. All six catalysts were commercially chemical compounds available from Sigma-Aldrich Co.

TABLE 1

| | $Ti(OCH_3)_4$ | $Sb(OCH_3)_3$ | $Ge(OCH_3)_4$ | $Al(OCH_3)_3$ | $Cu(OCH_3)_2$ | $B(OCH_3)_3$ |
|---|---|---|---|---|---|---|
| Melting Point (° C.) | 210 | 123-127 | −18 | 154 | 206 | −34 |
| Boiling Point (° C.) | 243 | — | 66 | 320 | — | 68-69 |
| Physical State @ Room Temperature | Solid | Solid | Liquid | Solid | Solid | Liquid |
| Solubility in Oil or Alcohol | Partial Soluble | Partial Soluble | — | Partial Soluble | Partial Soluble | — |

The data show that the Ti, Sb, Al and Cu based catalysts are solids at room temperature with melting points ranging from 125 to 210° C., except $B(OCH_3)_3$ and $Ge(OCH)_4$, which partially soluble in the oil or alcohol including methanol. Experimental results show that the quantities of $M(OCH_3)_x$ used in the process are within the solubility limits of the $M(OCH_3)_x$ used in the oil feeds and/or alcohols, so they remain in the liquid solution throughout the process loop in a continuous process without precipitating from the solutions.

Based on the experimental data for the above described species, it is expected that other organo-metallic compounds can be used to generate biodiesel through transesterification as well. In general it is expected that organo-metallic compounds having the formula: $M(OCH_3)_x$ wherein M is metal that is selected from the group consisting of B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4, will exhibit sufficient catalytic activities. A mixture of two or different organo-metallic compounds can be used.

One advantages of using $B(OCH_3)_3$ and $Ge(OCH_3)_4$ as the homogeneous catalyst is their, low boiling points of 68 and 66° C., respectively. With low boiling points, the catalysts circulated in process the loop with access amounts of alcohol, preferably methanol (boiling point 65° C.) thereby affording easy recovery and recycling of the catalyst for reuse. $B(OCH_3)_3$ is particularly preferred because of its low toxicity and relatively low cost.

FIG. 1 shows a simple process scheme, that is particularly suited with the low-boiling catalysts, and which includes multiple stirred tank reactors arranged in series and with each reactor associated with a flash drum and a decanter for reactor effluent separation. As illustrated, a vegetable oil feed 1 is fed into a first stirred tank reactor 100 and a mixture of alcohol and a homogeneous catalyst, such as $B(OCH_3)_3$) or $Ge(OCH_3)_4$, is recycled from tank 104 into reactor 100 via line 5. In reactor 100, the transesterification reaction between the vegetable oil and the alcohol is catalyzed by the low-boiling catalyst which is typically 0.1 to 20 wt % and preferably 5 to 10 wt % of the reactor mixture. The reactor temperature is in the range of 50-300° C., preferably 100-250° C., and more preferably 130-230° C., and the pressure is in the range of 0-20 bar and preferably 2.5-15 bar. The oil-to-alcohol mole ratio varies in the range of 0.1 to 30, preferably 0.5 to 20, and more preferably 1 to 10. The residence time in the reactor is from 0.5 to 5 hours and preferably from 1 to 3 hours. The oil-to-alcohol ratio and the oil feed rate (which is related to the oil residence time in the reactor) are adjusted to preferably achieve an 80 to 90% conversion of the oil feed.

Since the low-boiling catalyst is not consumed, it can be recycled for reuse and it is possible to use a higher catalyst circulation rate to promote the transesterification reaction and thus enhance the conversion of oil feed. In addition, a higher circulation rate also improves the solubility of the alcohol in the oil phase which further increases the oil conversion by improving the mass transfer rate.

Effluent from reactor 100 is transferred to a flash drum 106 via line 2; vaporized alcohol and catalyst flow through the overhead and is condensed in condenser 114 before entering tank 104 via line 3. A liquid mixture containing biodiesel (alkyl ester of fatty acid), glycerol, and unconverted oil feed is withdrawn from the bottom of flash drum 106 and fed to decanter 108 via line 4. A crude biodiesel phase containing unconverted oil feed is removed from the top of decanter 108 and fed to a second stirred tank reactor 102 via line 7 while the glycerol phase is withdrawn from the bottom as a glycerol by-product through line 8.

A mixture of alcohol and catalyst recycled from tank 104 is fed via line 6 to a second stirred tank reactor 102 where the alcohol reacts with the unconverted oil feed in the crude biodiesel, at a temperature and a pressure that are similar to those in the first reactor 100. The mixture is preferably supplemented with a fresh alcohol feed 9 and a make-up catalyst feed 10. The oil-to-alcohol ratio and the oil feed rate (related to oil residence time in the reactor) are adjusted in reactor 102 to achieve substantially complete conversion of the oil feed.

Effluent from reactor 102 is transferred to flash drum 110 via line 11 where the vaporized alcohol and catalyst from overhead is condensed in condenser 116 and fed to tank 104 via line 12. A liquid mixture of biodiesel (alkyl ester of fatty acid) and glycerol is withdrawn from the bottom of flash drum 110 and fed to decanter 112 via line 13. In the decanter, the phase containing purified biodiesel is removed from the top via line 14 as the purified biodiesel product while glycerol phase is withdrawn from the bottom as the glycerol by-product through line 15.

Figure 2:
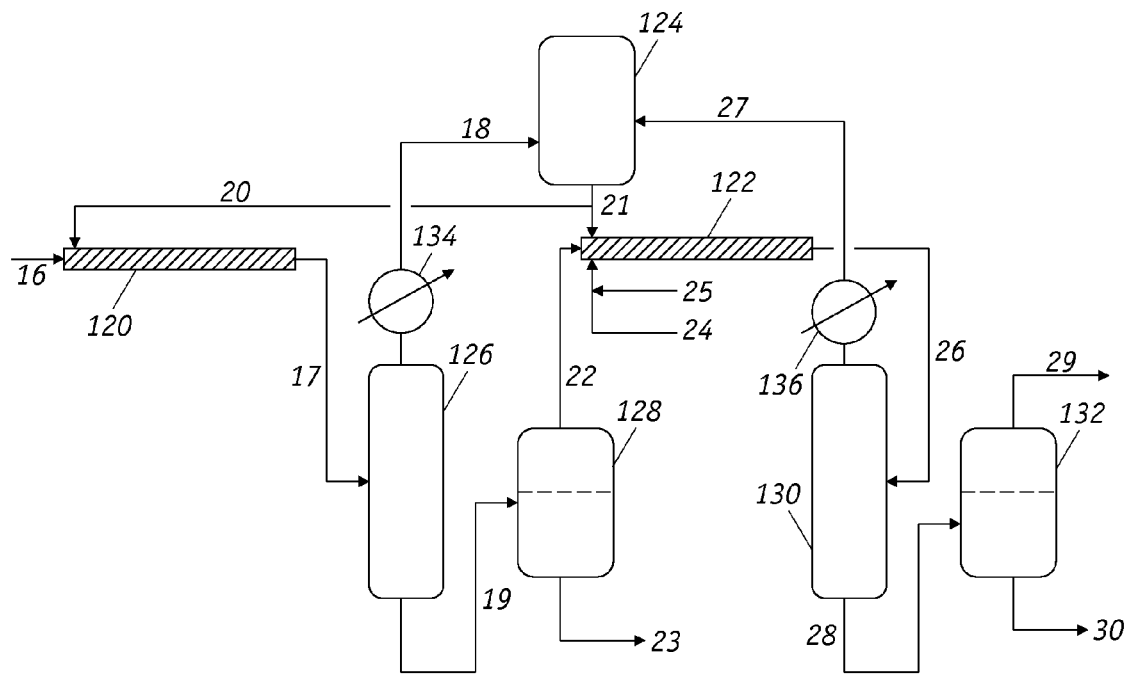

FIG. 2 illustrates a process scheme employing multiple tubular reactors (preferably packed with static mixers) configured in series with each reactor associated with a flash drum and a decanter for reactor effluent separation. In this process, vegetable oil 16 is fed into a first tubular reactor 120 while a mixture of alcohol and low-boiling homogeneous catalyst is recycled from tank 124 is fed into reactor 120 via line 20. The vegetable oil contacts the alcohol and homogeneous catalyst co-currently to carry out the transesterification reaction to produce biodiesel. The temperature of the reaction is maintained in the range of 50-300° C., preferably 100-250° C., and more preferably 130-230° C., and the pressure is maintained in the range of 0-20 bar and preferably 2.5-15 bar. The oil-to-alcohol mole ratio varies in the range of 0.1 to 30, preferably 0.5 to 20, and more preferably 1 to 10. The residence time in the reactor is from 0.5 to 5 hours and preferably from 1 to 3 hours. The oil-to-alcohol ratio and the oil feed rate (related to oil residence time in the reactor) are preferably adjusted to achieve 80 to 90% conversion of the oil feed. The concentration of catalyst in reactor 120 is in the range of 0.1 to 20 wt % of the reactor mixture and preferably 5 to 10 wt %.

Effluent from reactor 120 is transferred to flash drum 126 via line 17 wherein the alcohol and the catalyst vaporize through the overhead before being condensed in condenser 134 and introduced into tank 124 via line 18. A liquid mixture of biodiesel, glycerol, and unconverted oil feed is withdrawn from the bottom of flash drum 126 and fed via line 19 into decanter 128. The crude biodiesel phase containing unconverted oil feed is removed from the top of decanter 128 and fed to second tubular reactor 122 via line 22 while the glycerol phase is withdrawn from the bottom of decanter 128 as the glycerol by-product through line 23.

A mixture of alcohol and catalyst recycled from tank 124 is fed via line 21 into reactor 122. The recycled feed is preferably supplemented with a fresh alcohol feed 24 and a make-up catalyst is feed 25, into reactor 122. In reactor 122, the crude biodiesel containing unconverted oil feed contacts the alcohol and the homogeneous catalyst co-currently to produce biodiesel. The second reactor temperature and pressure are similar to those of first reactor 120. The oil-to-alcohol ratio and the oil feed rate (related to oil residence time in the reactor) are preferably adjusted in reactor 122 to achieve substantially complete conversion of the oil feed.

Effluent from reactor 122 is transferred via line 26 to flash drum 130 where the alcohol and catalyst are vaporized through the overhead and later condensed condenser 136 and introduced into tank 124 via line 27. A liquid mixture of biodiesel and glycerol from the bottom of flash drum 130 is fed to decanter 132 via line 28. A phase containing purified biodiesel is removed from the top of decanter 132 via line 29 as the purified biodiesel product while the glycerol phase is withdrawn from the bottom of decanter 132 as the glycerol by-product through line 30.

Figure 3:
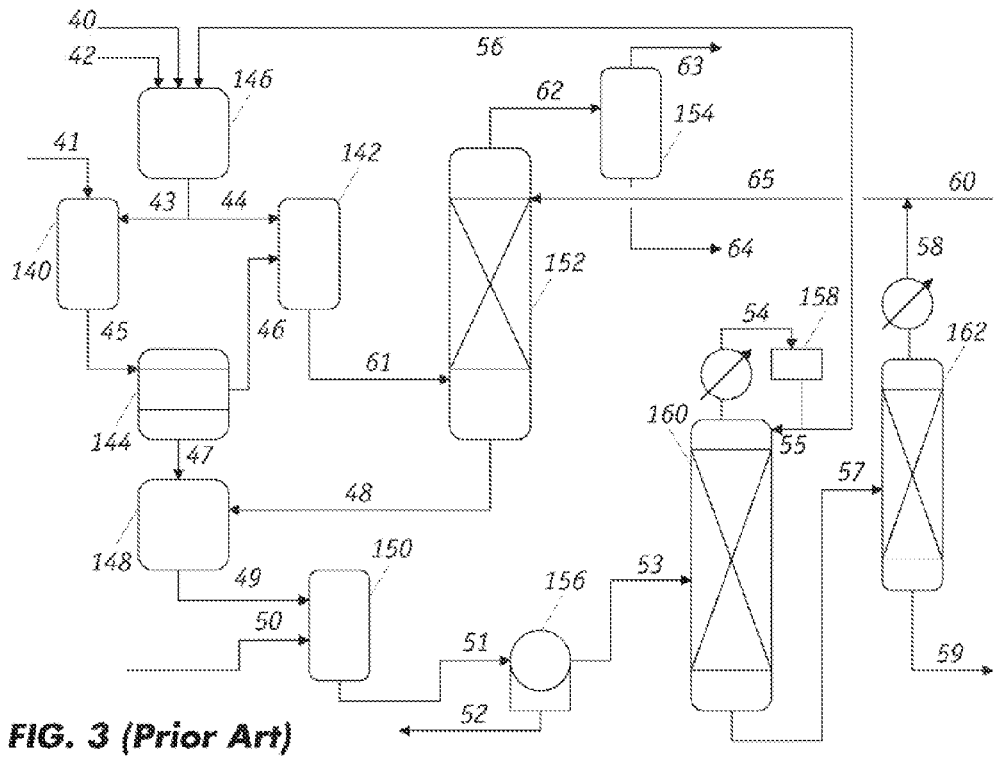
FIG. 3 shows a commercial transesterification process for biodiesel production using NaOH or KOH homogeneous catalyst.

FIG. 3 is a schematic diagram of a biodiesel process using homogeneous NaOH or KOH catalyst. The process scheme includes three major sections: (1) transesterification reaction section comprising mixing tank 146, first stage reactor 140, second stage reactor 142, and decanter 144; (2) glycerol phase separation section comprising mixing tank 148, neutralization reactor 150, filter 156, recovery column 160, and stripping column 162; and (3) ester phase purification section comprising extraction column 152 and vacuum dryer 154.

As illustrated, basic catalyst via line 40, fresh methanol feed via line 42 and recycled methanol via line 56 are mixed in tank 146 to completely dissolve the basic catalyst. A homogeneous mixture is withdrawn from tank 146 into a first-stage reactor 140 via line 43 while a vegetable oil feed 41 is introduced through the top the first-stage reactor 140. Reaction effluent with 90 to 92% oil conversion is withdrawn from the bottom of reactor 140 and transferred to decanter 144 via line 45 to separate the biodiesel (oil) phase and the glycerol phase. Phase separation may become slow or even difficult if the FFA and water contents in the oil feed are too high thereby causing a saponification reaction between the FFA and NaOH (or KOH). FFA and water contents in a desirable oil feed should be less than 0.5 and 0.05 wt %, respectively. In addition, high FFA levels in the oil feed will consume excess amounts of NaOH (or KOH) through acid-base neutralization reactions which produce salts which must to be water washed and removed from the product streams.

An oil phase from decanter 144 is transferred to the second-stage reactor 142 via line 46 which reacts with additional methanol which is fed to the reactor 142 via line 44, to achieve 99% or higher oil conversion. Effluent from reactor 142 is then fed via line 61 to extraction column 152 where it is washed counter currently with water; the washed biodiesel is withdrawn from the top via line 62 and dried in vacuum dryer 154. Dried biodiesel product is withdrawn through line 64 whereas vaporized moisture and light impurities are purged through line 63.

A glycerol phase from decanter 144 in line 47 and a spent wash water from the bottom of column 152 in line 48 are mixed in tank 148 before the mixture is transferred to neutralization reactor 150 via line 49 where the mixture reacts with phosphoric acid ($H_3PO_4$) from line 50. The neutralized effluent from reactor 150 in line 51 is filtered by filter 156 to remove the salt precipitation ($Na_3PO_4$ or $K_3PO_4$) which is disposed through line 52, while the filtrate is fed to recovery column 160 through line 53. A stream rich in glycerol is withdrawn from the bottom of via line 57 and transferred to stripping column 162 whereas a vapor stream rich in methanol is removed from the top via line 54 where it is condensed before entering accumulator 158. From accumulator 158, a portion of the condensate is recycled back to column 160 as reflux via line 55 and the remaining portion is recycled to tank 146 via line 56. Stripping column 162 removes the final moisture from the glycerol through the top of the column; the condensed moisture in line 58 is mixed wash water in line 60. A mixed water stream is fed to the upper portion of extraction column 152 through line 65. A dried glycerol by-product is withdrawn from the bottom of column 162 through line 59.

The conventional transesterification process as illustrated in FIG. 3 using basic or acid homogeneous catalyst to produce biodiesel from a vegetable oil is a complicated process than that of the present invention which uses the novel recyclable catalysts. The inventive process is simpler and does not need to contend with phase separation, acid-base neutralization, salt filtration, and waste disposal. In a continuous biodiesel producing process, the neutral low-boiling homogeneous organo-metallic catalysts of the present invention will exhibit a significantly higher catalytic activity for transesterifying vegetable oil or fat into biodiesel as compared to conventional base or acid homogenous catalysts. In addition, the continuous process of the present invention employs a non-corrosive process system due to the organo-metallic catalyst's neutral property. The catalyst and product can be readily separated due to the catalysts' low boiling points and the catalysts can be recycled for reuse due to their low boiling points and high stabilities.

The transesterfication reaction of the present invention can also be effected in a batch reactor such as an autoclave. The reactor is typically operated at a pressure of 0-20 bar and preferably from 2.5 to 15 bar to carry out the transesterification reactions at temperatures in the range of 50-300° C., preferably from 100-250° C., and more preferably from 130-230° C. The reaction time ranges from 0.1 to 20 hours, preferably from 0.5 to 5 hours, and more preferably from 1 to 3 hours. The oil-to-alcohol mole ratio is in the range of 0.1 to 30, preferably 0.5 to 20, and more preferably 1 to 10. As is the case with a continuous process, the alcohol is selected from $C_1$ to $C_6$ mono-alcohols, with methanol being preferred. No solvent is required.

The homogeneous catalysts of the present invention can use conventional vegetable oils, animal oils and fats and waste cooking oils, collectively referred to as oils. Preferred oils comprise soybean oil, palm oil, coconut oil, rapeseed oil, cottonseed oil, linseed oil, caster oil, peanut oil, olive oil, safflower oil, evening primrose oil, borage oil, carboseed oil, animal tallow, animal fat, and mixtures thereof. The oil typically has an acid number of from 0.5 to 20. The oil can contain high levels of water of 3 wt % or higher.

EXAMPLES

The catalytic activities of $KBH_4$, $B(OCH_3)_3$, $M(OCH_3)_x$ were compared.

Example 1

Catalytic Activity of Homogeneous $KBH_4$ Catalyst 134 grams of soybean oil and 28 grams of methanol (under oil-to-methanol mole ratio (O/M) of 1:6), and 1.6 grams of $KBH_4$ were added to an autoclave. The transesterification reaction was conducted under 250 rpm mixing rate at 60° C. and 1.0 bar for two hours and the conversion was analyzed by gas chromatography (GC).

Under the above reactor conditions, it was demonstrated that the catalytic activity of $KBH_4$ is comparable to that of the conventional strong base catalyst, NaOH, with a conversion of 93%. The advantages of using $KBH_4$ catalyst over using NaOH catalyst include exposing the process equipment to less corrosive environment and easy of phase separation between bio-diesel and glycerol (which a potential problem associated with the NaOH catalyst) by avoiding the occurrence soponification reaction in the reaction mixture.

Figure 4:
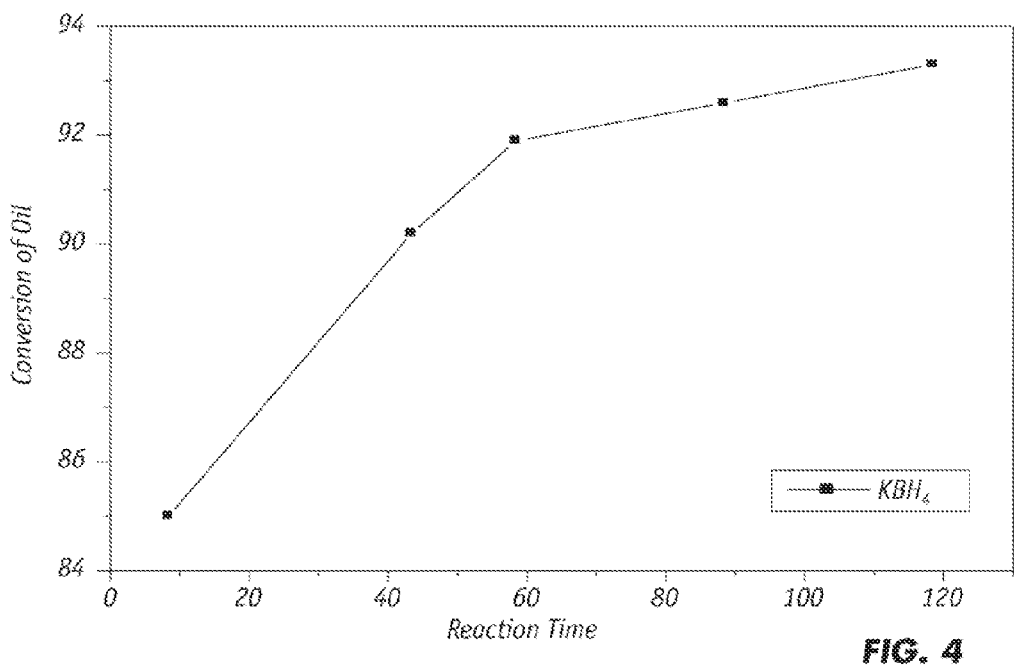
FIG. 4 compares the conversion of soybean oil versus transesterification reaction time with homogeneous $KBH_4$ catalyst at 60° C. under an oil-to-methanol mole ratio (O/M) of 1:6.

The relationship of transesterification conversion catalyzed by $KBH_4$ catalyst versus reaction time is presented in FIG. 4 which shows that the conversion is directly proportional to the reaction time up to two hours. This suggests that conversion higher than 93% can be achieved when the reaction time is longer than two hours.

Example 2

Catalytic Activity of Homogeneous $B(OCH_3)_3$ Catalyst

It is shown that $B(OCH_3)_3$ can be generated through the reaction of $KBH_4$ and $CH_3OH$ as expressed in Reactions (1) and (2). Therefore, at least a part of catalytic activity of $KBH_4$ for transesterification reaction demonstrated in Example 1 can be attributed to the presence of $B(OCH_3)_3$ species that are generated in the autoclave during the experimental run. The other part of the activity can be caused by $KOCH_3$, a weak base catalyst. To determine the activity of $B(OCH_3)_3$, an experimental run was conducted by using $B(OCH_3)_3$ directly for catalyzing the transesterification reaction of a vegetable oil with methanol. In particular, 134 grams of soybean oil and 28 grams of methanol (under O/M of 1:6), and 5 wt % $B(OCH_3)_3$ were added to the autoclave. The transesterification reactions were conducted under a mixing rate of 250 rpm, pressure of 14.6 bar and temperatures of 130° C., 180° C. and 230° C. for two hours.

Figure 5:
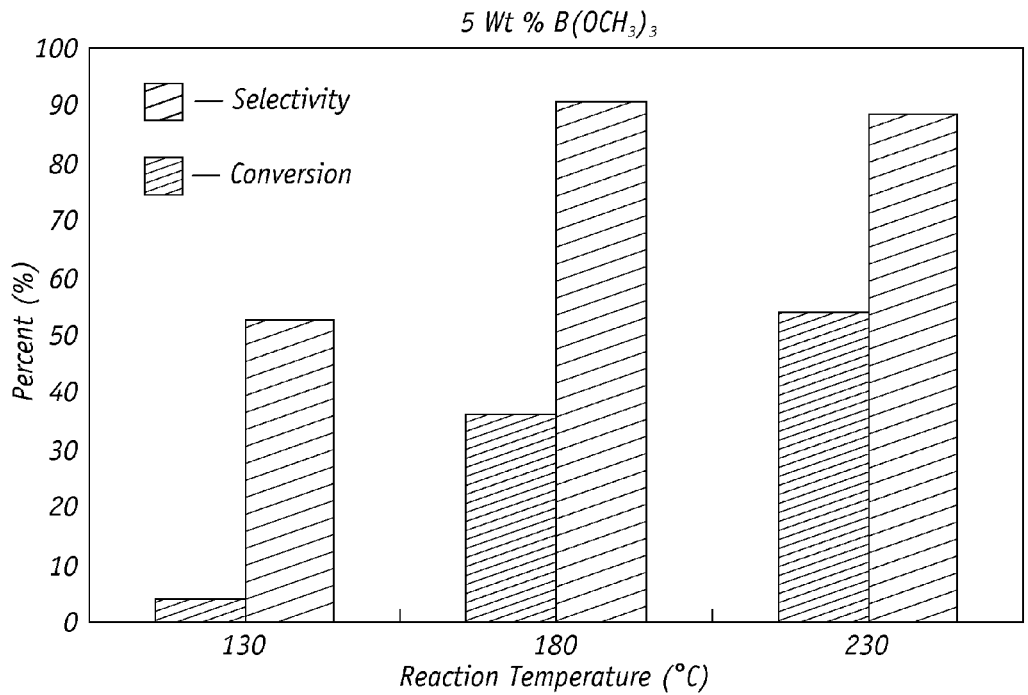
FIG. 5 compares the conversion and selectivity of soybean oil versus transesterification reaction temperature with homogeneous $B(OCH_3)_3$ catalyst under an O/M of 1:6.

The conversion and catalyst selectivity at different temperatures were determined by GC analysis of reactor effluent and presented in FIG. 5 which shows that the $B(OCH_3)_3$ catalyst can achieve 7% conversion with 50% selectivity at 130° C. However, both conversion and selectivity increased significantly to 54% and 90%, respectively, when the reaction temperature was increased to 230° C. The data confirm that $B(OCH_3)_3$ does have significant catalytic activity for converting vegetable oil into biodiesel. Additional experimental runs under various conditions were carried out to optimize the performance of $B(OCH_3)_3$ in the autoclave. A conversion of 60% with 84% selectivity was observed under an O/M ratio of 1:6 and a reaction temperature of 230° C. It is not surprising that, under the same O/M and reaction time, $KBH_4$ is more active than $B(OCH_3)_3$ at even lower temperatures, because it generates two catalytic species, namely: ($B(OCH_3)_3$ and $KOCH_3$), that catalyze the transesterification reaction. However, as mentioned earlier, $KBH_4$ has the same drawback as the conventional basic catalyst because the existence of $KOCH_3$.

Since $B(OCH_3)_3$ is not consumed in the reaction and can be recycled for reuse, larger amounts of the catalyst can be mixed into the methanol feed to raise its solubility in the oil phase. This leads to enhanced mass transfer rates as well as achieving essentially 100% catalytic conversion of the oil feed into biodiesel in a process with multi-stage stirrer tank reactors or multi-stage tubular reactors Again, it was observed that phase separation between bio-diesel and glycerol was readily achieved and facilitated by avoiding soponification in the reaction mixture, which would otherwise occur if a basic catalyst were used.

Example 3

Catalytic Activity of Homogeneous $M(OCh_3)_x$ Catalysts

Various species of $M(OCH_3)$ homogeneous catalysts for directly catalyzing the transesterification reaction of a vegetable oil with methanol were conducted. Specifically, a mixture containing 67 grams of soybean oil and 28 grams of methanol under an oil-to-methanol of 1:12 was added to an autoclave along with a predetermined amount of a homogeneous catalyst of $M(OCH_3)_x$. The transesterification reaction was conducted for two hours under mixing rate of 200 rpm, a temperature 200° C. and atmospheric pressure. The conversion and catalyst selectivity were determined by GC analysis of reactor effluent and are summarized in Table 2.

TABLE 2

|  | $Ti(OCH_3)_4$ | $Sb(OCH_3)_3$ | $Ge(OCH_3)_4$ | $Al(OCH_3)_3$ | $Cu(OCH_3)_2$ |
|---|---|---|---|---|---|
| Catalyst (gm) | 0.5 | 0.5 | 2.3 | 1.0 | 0.5 |
| Conversion (wt %) | 99.07 | 96.44 | 99.84 | 3.83 | 34.88 |
| Selectivity (wt %) | 93.72 | 85.80 | 95.80 | 47.19 | 40.45 |

Figure 6:
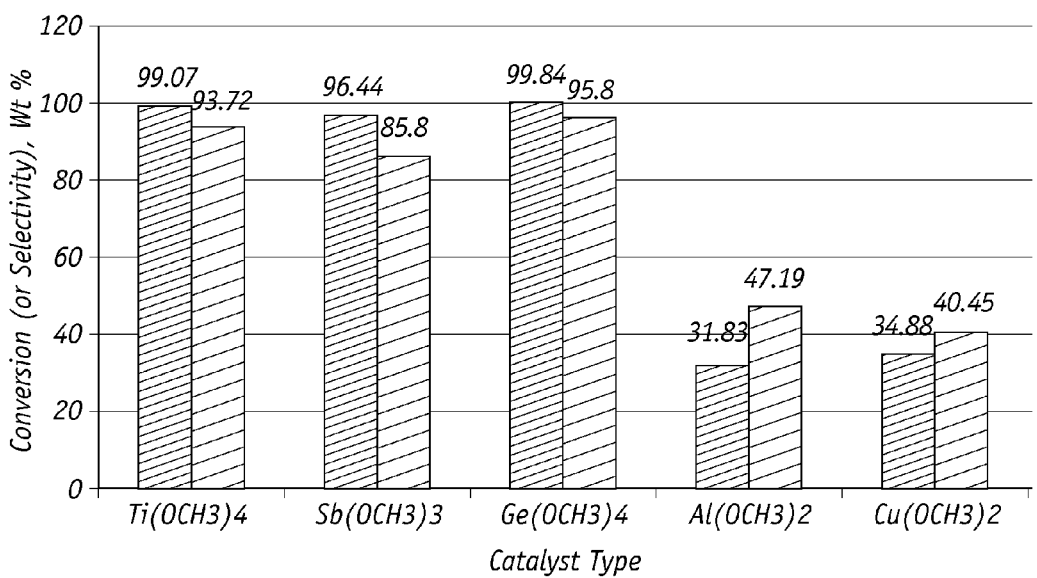
FIG. 6 compares the conversion and selectivity of transesterification reaction of soybean oil versus different homogeneous $M(OCH_3)_4$ catalysts under an O/M of 1:12.

As shown, the conversion and selectivity under $Ti(OCH_3)_3$ are quite impressive, 99.07 and 93.72 wt %, respectively. The catalysts $Sb(OCH_3)_4$ and $Ge(OCH_3)_4$ also performed well as compared to the conventional basic catalyst NaOH (or KOH) whereas $Al(OCH_3)_3$ and $Cu(OCH_3)_2$ showed relatively poorer performance. The conversion and selectivity are also presented graphically in FIG. 6. Again, for each catalyst it was observed that phase separation between bio-diesel and glycerol was readily achieved by avoiding the occurrence soponification reaction in the reaction mixture. This example demonstrates that the functional group —$OCH_3$ in the homogeneous catalyst of $B(OCH_3)_3$ or $M(OCH_3)_x$ is critical to the catalytic activity of transesterification reaction between vegetable oil or animal fat with the alcohol to produce biodiesel.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A process for producing biodiesel through transesterification that comprises:
   contacting a triglyceride-containing vegetable or animal oil with an aliphatic mono-alcohol containing 1 to 6 carbon atoms and a homogeneous catalyst to effect transesterification to yield a mixture containing a fatty acid alkyl ester and glycerol wherein the homogenous catalyst is a non-basic and non-acidic organo-metallic compound having the formula: $M(OCH_3)_x$ wherein M is metal that is selected from the group consisting of B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4.

2. The process of claim 1 wherein the homogenous catalyst is selected from the group consisting of $B(OCH_3)_3$, $Ti(OCH_3)_4$, $Sb(OCH_3)_3$, $Ge(OCH_3)_4$, $Al(OCH_3)_3$, $Cu(OCH_3)_2$, and mixture thereof.

3. The process of claim 1 wherein the homogenous catalyst is $B(OCH_3)_3$.

4. The process of claim 1 wherein the alcohol is methanol.

5. The process of claim 1 wherein the oil is selected from a group consisting of soybean oil, palm oil, coconut oil, rapeseed oil, cottonseed oil, linseed oil, caster oil, peanut oil, olive oil, safflower oil, evening primrose oil, borage oil, carboseed oil, animal tallow, animal fat, and mixtures thereof.

6. The process of claim 5 wherein the oil has an acid number of from 0.5 to 20.

7. The process of claim 1 wherein the oil-to-alcohol mole ratio is from 0.1 to 30.

8. The process of claim 1 wherein contacting occurs in a reactor and the contacting time ranges from 0.5 to 5.0 hours.

9. The process of claim 1 wherein contacting occurs in a reactor and the homogenous catalyst comprises 5 to 10 wt. % of the total oil and alcohol that is charged in the reactor.

10. The process of claim 1 wherein the contacting occurs at a temperature of between 100° C. and 250° C. and a pressure of between 0 to 20 bar.

11. A continuous process for producing biodiesel through transesterification which comprises:
   a. introducing an oil feed and a first alcohol/catalyst mixture, which comprises an aliphatic mono-alcohol containing 1 to 6 carbon atoms and a homogenous catalyst that is a non-basic and non-acidic organo-metallic compound having the formula: $M(OCH_3)_x$ wherein M is metal that is selected from the group consisting of B, Na, Mg, K, Ca, Sc, Ti, V, Cr, Mn, Fe, Co, Ni, Cu, Zn, Ga, Ge, Al, Sn, Sb, Mo, Ag, and Cd and x is an integer from 2, 3 or 4, into a first reactor and to effect transesterification to yield a first effluent containing a fatty acid alkyl ester, glycerol, alcohol and homogenous catalyst;
b. removing alcohol and homogenous catalyst from the first effluent and recovering a first biodiesel phase comprising the fatty acid alkyl ester and a first glycerol phase;
c. introducing the first biodiesel phase, a second alcohol/catalyst mixture which comprises the aliphatic monoalcohol and the homogenous catalyst, and optionally fresh alcohol and optionally fresh homogenous catalyst into a second reactor to effect transesterification to yield a second effluent containing the fatty acid alkyl ester, glycerol, alcohol and homogenous catalyst; and
d. removing alcohol and homogenous catalyst from the second effluent and recovering a purified biodiesel phase comprising the fatty acid alkyl ester and a second glycerol phase.

12. The process of claim 11 wherein step b comprises the steps of:
   i. transferring the first effluent to a first flash drum and recovering a first vapor mixture of alcohol and homogenous catalyst and withdrawing a first liquid mixture comprising the fatty acid alky ester and glycerol; and
   ii. condensing the first vapor mixture and transferring the condensate to a mixing tank, which supplies the first alcohol/catalyst mixture in step a and the second alcohol/catalyst mixture in step c.

13. The process of claim 11 wherein step d comprises the steps of:
   i. transferring the second effluent to a second flash drum and recovering a second vapor mixture of alcohol and homogenous catalyst and withdrawing a second liquid mixture comprising the fatty acid alkyl ester and glycerol;
   ii. condensing the second vapor mixture and transferring the condensate to the mixing tank; and
   iii. recovering the fatty acid alkyl ester from the second liquid mixture.

14. The process of claim 1 wherein the homogenous catalyst is selected from the group consisting of $B(OCH_3)_3$, $Ti(OCH_3)_4$, $Sb(OCH_3)_3$, $Ge(OCH_3)_4$, $Al(OCH_3)_3$, $Cu(OCH_3)_2$, and mixture thereof.

15. The process of claim 11 wherein the homogenous catalyst is $B(OCH_3)_3$.

16. The process of claim 11 wherein the alcohol is methanol.

17. The process of claim 11 wherein the oil is selected from a group consisting of soybean oil, palm oil, coconut oil, rapeseed oil, cottonseed oil, linseed oil, caster oil, peanut oil, olive oil, safflower oil, evening primrose oil, borage oil, carboseed oil, animal tallow, animal fat, and mixtures thereof.

18. The process of claim 17 wherein the oil has an acid number of from 0.5 to 20.

19. The process of claim 11 wherein the oil-to-alcohol mole ratio in the first and second reactors is from 0.1 to 30.

20. The process of claim 11 wherein the reaction time in the first and second reactors ranges from 0.5 to 5.0 hours.

21. The process of claim 11 wherein the homogenous catalyst comprises 5 to 10 wt. % of the total oil and alcohol that is charged in each of the first and second reactors.

22. The process of claim 11 wherein the first and second reactors are operated at a temperature of between 100° C. and 250° C. and a pressure of between 0 to 20 bar.

* * * * *